United States Patent [19]

Linkow et al.

[11] Patent Number: 4,944,754

[45] Date of Patent: Jul. 31, 1990

[54] METHOD OF MANUFACTURING SYNTHETIC BONE COATED SURGICAL IMPLANTS

[75] Inventors: Leonard I. Linkow, New York, N.Y.; Anthony J. Armini, Bedford, Mass.; Anthony W. Rinaldi, Philadelphia, Pa.

[73] Assignee: Vent-Plant Corporation, Philadelphia, Pa.

[21] Appl. No.: 193,505

[22] Filed: Apr. 26, 1988

Related U.S. Application Data

[63] Continuation-in-part of Ser. No. 43,908, Apr. 29, 1987.

[51] Int. Cl.[5] .............................................. C23C 14/46

[52] U.S. Cl. ................................ 623/16; 204/192.11; 204/298.04; 433/201.1; 623/66

[58] Field of Search ...................... 204/192.15, 192.11, 204/298.04; 427/2; 623/16, 66; 433/201.1

[56] References Cited

PUBLICATIONS

John L. Vossen, Thin Film Processes, Academic Press, New York, 1978, pp. 14–17, 42–45, 175–198.

Brian Chapman, Glow Discharge Sputtering Processes, John Wiley & Sons, New York, 1980.

Kent, J. N. et al. (Abstracts from the 12th Annual Meeting of the Society for Biomaterials, p. 16, 1986).

Thomas, K. A. et al. (Abstracts from the 12th Annual Meeting of the Society for Biomaterials, p. 15, 1986).

Kay, J. F. et al. (Abstract from the 12th Annual Meeting of the Society for Biomaterials, p. 13, 1986).

Cook, S. D. (Int. J. Oval and Maxillofacial Implants, 27: 15–22, 1987).

Lacefield, W. R. (Abstract from the 12th Annual Meeting of the Society for Biomaterials, p. 12, 1986).

*Primary Examiner*—John F. Niebling

*Assistant Examiner*—William T. Leader

*Attorney, Agent, or Firm*—Darby & Darby

[57] ABSTRACT

A process is provided for depositing hydroxylapatite on the surface of materials suitable for implantation into animals and humans. In this process, a coating of hydroxylapatite is applied to dental or surgical implants using a sputter technique that employs a high energy ion beam and a negative potential to coat the implant. The process is carried out in a vacuum into which a controlled amount of oxygen is introduced.

16 Claims, 1 Drawing Sheet

18 300V − + 16 17 30 33 0+ 0+ 0+ 32 11 10 e e e 31 12 26

METHOD OF MANUFACTURING SYNTHETIC BONE COATED SURGICAL IMPLANTS

BACKGROUND OF THE INVENTION

This application is a continuation-in-part pending of U.S. Patent Application Ser. No. 043,908 filed Apr. 29, 1987 of Leonard I. Linkow et al. The entire disclosure of said application is incorporated herein by reference.

This invention relates to a novel method of manufacturing a synthetic bone-coated material useful for surgical and dental implants.

The mineral fraction of bones and teeth in vertebrates is composed largely of apatites (chemical formula $Ca_{10}(PO_4)_6OH_2$) in addition to carbonate, fluoride, hydroxide, and citrate. Bone crystals belong to the group of hydroxylapatites (HA). These crystals are platelets, or rods, about 8 to 15 angstroms thick, 20–40 angstroms wide, and about 200–400 angstroms long, with a density of about 3.0. This inorganic crystal structure imparts to bone an elastic modulus similar in strength to that of concrete.

Synthetic hydroxylapatites have been developed and used for a variety of surgical purposes, e.g. to fill bone cavities and to promote the growth of new bone about HA fragments. Also, HA coatings have been formed on implant materials to promote the anchoring of the implant to the bone.

The use of HA coatings for biological implants offers several advantages. Hydroxylapatite (HA) has demonstrated its ability to enhance its integration into bone due to the fact that it biologically binds to natural bone. The deposition of new bone occurs on the HA coating itself leading to a significant increase in the rate at which the surgical site heals.

J. N. Kent (*Abstracts from the 12th Annual Meeting of the Society for Biomaterials,* pp. 16, 1986) evaluated the efficacy of HA-coated and non-coated dental implants in dogs. Titanium cylindrical dental implants were coated with a fifty micron thick layer of HA and compared with non-HA coated titanium implants when placed in the anterior mandible and maxilla teeth for 12 weeks. Kent found that none of the non-coated materials adhered to the adjacent bone, whereas 100% of the HA-coated implants were adherent and could not be removed from the bone. The HA-coated implants demonstrated an intimate bone-implant interface without intervening fibrous tissue. The HA-coated dental implants thus provided an increased stability and retention compared to polished and grit surfaced cylindrical titanium dental implants.

Various techniques are known for the deposition of HA onto surfaces for use as biological implants. Thomas et al. (*Abstracts from the 12th Annual Meeting of the Society for Biomaterials,* pp. 15, 1986) disclosed that plasma-sprayed, HA-coated porous titanium hip implants that were inserted into adult mongrel dogs demonstrated increased amounts of bone ingrowth as compared to non-HA coated implants. The coating was sintered HA about 50 microns thick, applied using a plasma spray technique. The bone adjacent to the HA-coated implant also appeared to be better organized and had a higher degree of mineralization than bone adjacent to control implants which lacked the HA coating.

Kay et al. (*Abstracts from the 12th Annual Meeting of the Society for Biomaterials,* pp. 13, 1986) disclosed the use of HA-coated smooth titanium and cobalt-chrome-molybdenum (Co—Cr—Mo) implants using a modified plasma spray process. Kay et al. report that the coating was of a high density; however, the outermost 15–20% of the coating was less dense due to the nature of the deposition process.

W. R. Lacefield (*Abstracts from the 12th Annual Meeting of the Society for Biomaterials,* pp. 12, 1986) compared the coating of implants made of sintered alumina, titanium, or the alloys Ti—6A1—4V and Co—Cr—Mo by a dip process and by sputter coating process using an Argon beam in a vacuum chamber. The dipping process comprised a repeated dipping of the test specimens in a slurry containing 3–5 mesh HA powder followed by firing at 1100°–1200° C. for 1–3 hours. The sputter coating process was accomplished by cleaning the implants first using an Argon beam, followed by sputter coating using a 6 inch diameter rotating target of dense HA placed in the path of Argon having a typical energy of 2–3 kev. The sputter process was continued for 17–20 hours and produced a coating of 0.5–2.2 microns. Lacefield disclosed that dip coating had an adverse effect on the microstructure of the coated materials. This was due to an uncontrolled HA grain growth on the alumina, titanium and titanium alloy implants, and a massive carbide precipitation on the Co—Cr—Mo alloy implants. This led to low bone strengths and fracturing when the implant went from a high temperature (500° C.) to water. The sputter coated implant was said to have a uniform thickness, high integrity coating covering all topological features of the substrate. However, X-ray diffraction demonstrated that some of the sputter-coated implants had coatings which were not crystalline HA, but were primarily an amorphous calcium-phosphate layer.

SUMMARY OF THE INVENTION

All of the above techniques suffer from the disadvantage that they form a brittle layer of deposited material which can easily break off. Additionally, the production of a rough and irregular coating by the prior art techniques can lead to irritation of the tissue in the area where the implant is applied, if growth occurs there. Moreover, the prior art techniques cannot be applied to threaded implant configurations such as screws or total hip replacements.

Therefore, what is needed is an improved process for coating materials for use as implants which overcomes the drawbacks and difficulties mentioned above in these processes.

The present invention relates to an improved process for depositing HA on the surface of materials suitable for implantation into animals, particularly mammals (including humans). These materials, including but not limited to titanium alloys and cobalt-chrome-molybdenum alloys, are sputter coated with calcium hydroxylapatite using a high energy beam while a negative potential is applied to the implant material. This produces a coated surgical implant which is close to the proper hardness of natural bone and has an appropriate phosphate to calcium ratio. The HA is deposited as a thin layer which is not cracked or pitted.

In one embodiment, the present invention is used to apply a hydroxylapatite coating on dental or surgical implants. The high energy ion beam has between about 2 and about 200 kev of energy, the negative potential is between about 300 volts and about 1000 volts, and the entire process is conducted under a vacuum in the presence of a preselected amount of oxygen gas.

BRIEF DESCRIPTION OF THE DRAWING

The foregoing and other features of the present invention will be apparent to those of ordinary skill in the art in light of the present description, accompanying claims and appended drawings in which:

DETAILED DESCRIPTION OF THE INVENTION

Figure 1:
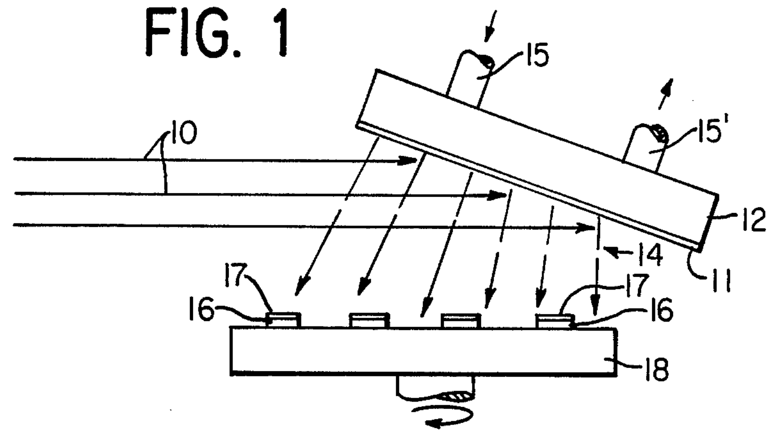
FIG. 1 is a drawing of the apparatus used in the practice of the present invention.

The present invention is directed to an improved process for depositing HA onto the surface of dental or surgical implants. The process employed for this coating is ion beam sputtering, which uses a high energy beam to "kick out" atoms from a HA plate and allows them to be directed onto the implant to be coated. The geometry of this set-up is shown in FIG. 1.

A 50 kev beam 10, preferably Xenon, is directed at an angled substrate or target 12 containing a coating 11 of sintered HA. The substrate 12 may be hollow and water cooled by a flow of water into conduit 15 and out of conduit 17, which are connected to the hollow interior of the substrate 12. The striking of the beam 10 onto the coating 11 leads to the sputtering of HA ions 14 out of the coating 11 onto the implants 16 which are to be coated. These parts are placed upon a rotating support platter 18 that may also be water cooled. The entire arrangement is located in a high vacuum into which a controlled amount of oxygen or, preferably, water vapor is bled. As a result, a thin coating 17 of HA is formed on the product. This sputter process may be utilized on implant materials that cannot survive the high temperatures of vacuum evaporation which has been used for coating materials with HA.

The high velocity imparted to the sputtered atoms through the use of a high energy Xenon beam directed at an HA target allows the atoms to penetrate into the surface of the implant to be coated and, therefore, provides a superior adhesion of HA to the implant over those produced using evaporative coating techniques. Xenon is preferred because it can produce a higher yield of sputtered HA than any other readily-available gas.

Xenon beam sputtering is a process that provides extremely high microscopic temperatures (high kinetic energy) while maintaining the macroscopic temperature of the bulk HA below its sublimation/decomposition point. Without this capability, less energy would be imparted to the target and thus the ions would not penetrate the surface of the device to be coated to the same extent. This would produce a coating that does not have the adherence of the present invention.

An alternative to the use of the Xenon beam includes, but is not limited to a Krypton beam. As used herein, high energy is defined as at least 2 kev and may extend up to 200 kev, but preferably is at least 10 kev.

The substrate or target 12 (FIG. 1) is covered with a suitable target coating material 11, preferably sintered HA. Alternative target coating materials include, but are not limited to, plasma sprayed HA and HA powder. The process is carried out in a high vacuum so that contaminant atoms cannot be incorporated into the coating. A high vacuum, as used herein, is defined broadly as at least $10^{-4}$ torr to $10^{-7}$ torr and preferably from $10^{-6}$ torr to $10^{-7}$ torr.

A proper stoichiometry of the HA compound is achieved by bleeding into the vacuum a precisely metered amount of oxygen or preferably water vapor such that OH groups are formed to replace some of the oxygen that is usually lost from the HA molecule while in transit to the metal substrate. The amount of oxygen to be used broadly falls within the range of between about $10^{-5}$ torr and about $10^{-6}$ torr, and preferably within the range of between about $3\times10^{-6}$ torr and about $9\times10^{-6}$ torr. The amount is related to the vacuum pressure used. The amount of water vapor to be used would be twice as much as the above-cited amounts for oxygen.

Figure 2:
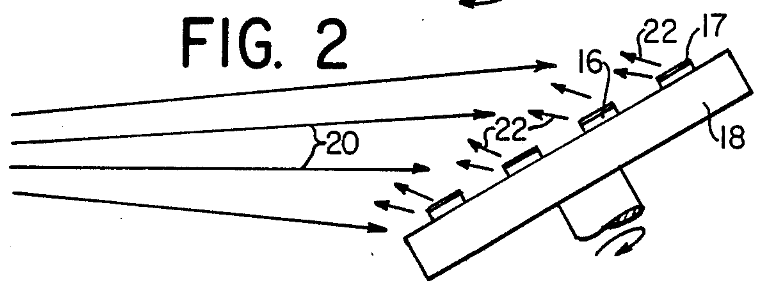
FIG. 2 is a drawing of the apparatus used to ion beam etch the material to be sputter coated.

Prior to the coating process, the metal substrate can first be sputter-etched or cleaned by directing the ion beam directly onto the metal surface to be coated. An arrangement for an apparatus to accomplish this is shown in FIG. 2. The entire operation is conducted in a vacuum upon a rotating water-cooled platter 18 (Model Z-100 ion implanter, available from Eaton Corp., Beverly, Mass.). Xenon atoms 20 are impelled onto the parts 16 to be coated. This action sputters off all surface oxides 22 and permits the HA molecules deposited as shown in FIG. 1 to adhere directly to the metal surface with no intervening oxide barrier.

Figure 3:
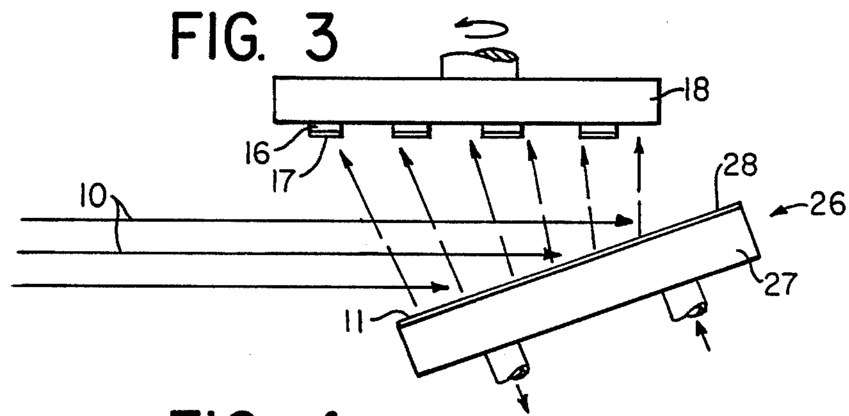
FIG. 3 is a drawing of the apparatus used in an alternative embodiment of the present invention.

An alternative to the deposition process of FIG. 1 is shown in FIG. 3. In this process, the target 26 and the parts 16 have been reversed in position so that the target is below the parts. The target in this arrangement is made in the form of a tray 27 supporting powdered HA 28, instead of sintered HA. Since the powder is loose and is not adhered to the target substrate 26, the creation of a target is simple and inexpensive. However, the target must be right side up or the powdered HA would fall off.

Because of the high energy of the Xenon beam, the HA ions are given sufficient energy to kick off the target against the force of gravity, reach the parts and still have sufficient velocity to penetrate the surface of the parts.

The principal uses of the present invention are for any application where live bone must grow toward and adhere to a foreign metal within the body of an animal or human to be treated. This includes total joint prostheses, dental implants, ear implants, and similar devices.

The advantages of the process of the present invention include the ability to coat a metal substrate with HA which is close to natural apatite ($Ca_{10}(PO_4)_6(OH)_2$). This is in part achieved through the introduction of OH ions into the atmosphere of the vacuum. In addition, crystal grains are not visible on the coating surface, thus leading to a featureless surface having a full density non-porous HA film. This eliminates the tendency of the film to crack when the implant is bent as is often necessary during installation. Also, the process leads to an excellent adhesion of the HA coating to titanium, stainless steel, cobalt-chrome-molybdenum and similar materials, while keeping the production costs at a minimum.

S. D. Cook et al. (*Int. J. Oral and Maxillofacial Implants,* 27: 15–22, 1987) disclosed that plasma sprayed HA coated titanium implants developed 5–8 times the mean interfacial strength of uncoated implants when implanted into adult mongrel dogs. Histological evaluations in all cases revealed mineralization of interface bone directly onto the HA-coated implant surface. However, push-out tests conducted at all times post-implantation demonstrated that failures occurred primarily at the HA-titanium interface. Therefore, HA-coated implants of the present invention can be further coated, using a conventional plasma spray or modified plasma spray process (such as those disclosed in U.S. Pat. No. 4,145,764 issued Mar. 27, 1979 and U.S. Pat. No. 4,223,412 issued Sept. 23, 1980, both incorporated herein by reference). This would provide a titanium implant with two layers of HA coating. The ion-implanted HA coating would act as an intermediate layer to effect a method of bonding subsequently plasma-sprayed HA coatings to titanium. The resultant implant would then have the advantages of superior biocompatability and superior adhesion of both methods.

The present inventors have found that in order to promote the proper crystalline growth of the HA film while it is being deposited, a continuous bombardment of the growing HA film during the coating by background $0_2$ ions is desirable.

The advantage of this technique, as described below, is that it promotes ionization of the background gas (oxygen) at high vacuums (pressures lower than $10^{-5}$ torr). This is achieved by combining the effects of:

(a) a 300–1000 volt negative potential on the implants to be coated, and (b) the Xenon beam directed on the target.

Neither of these effects alone will provide adequate bombardment of the film at high vacuums. The Xenon creates charged ion pairs in the oxygen background gas in front of the target, and the negative potential sweeps the positive ions over the implants. This phenomenon is not a conventional glow discharge because glow discharge exists only around negative electrodes at pressures between $10^{-2}$ and $10^{-4}$ torr.

In this embodiment of the present invention, the Xenon beam is required to cause ionization of the background gas at pressures between about $10^{-5}$ torr and about $10^{-7}$ torr, and preferably ranging between about $3\times10^{-6}$ torr and about $5\times10^{-6}$ torr. A lighter inert gas, such as Argon or Krypton, would not cause enough ionization at the pressures employed and a heavier gas, Radon, is radioactive and therefore not practical. Thus the use of Xenon is important to this embodiment of the invention.

The HA employed in this embodiment of the present invention can be either sintered or powdered, as described above. In addition, the implants to be coated may be sputter etched or cleaned, as described above, before coating.

Figure 4:
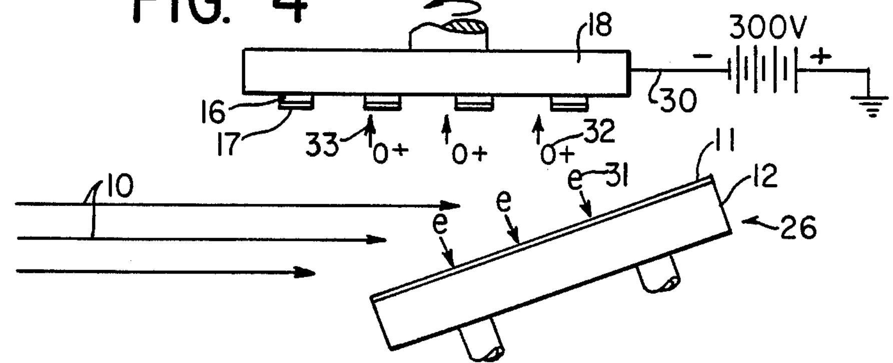
FIG. 4 is a drawing of the apparatus used in a further embodiment of the present invention.

Apparatus for practicing this embodiment of the present invention is shown in FIG. 4. In FIG. 4, the target 26 is bombarded by the high energy beam 10 (which has energy ranging between about 2 kev and about 200 kev) while a negative voltage source 30 (having an output of between about 100 volts and about 1000 volts) is applied to the parts 16 through support platter 18. This promotes ionization of the background oxygen gas 32 in front of the target 12 and causes the positive ions 33 to be kicked off of the target 12 and to be swept over the implants 16 which are to be coated.

The connection between bone and an implant can be improved by providing a porous surface on the implant into which new bone may grow. This may be accomplished by the present invention by sputter etching the implant to clean it and then sputter coating it with metal, e.g. titanium. This sputter coating is porous and promotes adhesion with new bone. However, the new bone will not attach to the metal as readily as when the metal is first given a thin coating of HA.

To provide an HA coating, the present ion beam sputtering process is used to cover the porous metal coating on the implant with an HA coating which extends into the pores, but does not fill them. As a result, there is a strong adhesion of a porous metal coating on the implant, a strong adhesion of an HA coating on the porous metal layer, and a strong attachment of new bone to the HA coating. Each of these layers is created without the intervening oxide layer typically formed with prior art processes. Thus, there is no tendency for the porous metal layer or the HA coating to chip off and cause failure of the anchoring of the implant in the bone.

The present invention is described further below in specific examples which are intended to illustrate it without limiting its scope.

EXAMPLE 1

The sputtering experiments described below were done using a modified ion implanter (Eaton Model Z-100, Eaton Corp., Beverly, Mass.).

The Xenon beam current on the water-cooled HA sputter target was approximately 2 mA over an area of approximately 16 in.$^2$ on the HA target. The samples were microscope glass slides, small (1 cm. diameter) stainless steel metal discs which were masked with a sheet of stainless steel foil to cover half of the exposed area, and sheets of titanium foil. Runs were performed using approximately 20 mA-hours of Xenon dose and using none, $3\times10^{-6}$ torr, and $6\times10^{-6}$ torr oxygen gas bled into the vacuum chamber.

The target was a copper plate 4 inches × 4 inches × ¼ inch thick, coated with approximately 75 microns of sintered HA (Coor's, Inc., Golden, Colo.).

The conditions for a series of three runs are shown in Table 1 below.

TABLE 1

| Run # | Xenon Beam Dose | $O_2$ Pressure | Samples |
|---|---|---|---|
| 1 | 20 mA-hrs. | 0 | 1-Glass Slide<br>1-Stainless Disk<br>1-Titanium Foil |
| 2 | 20 mA-hrs. | $3 \times 10^{-6}$ torr | 1-Glass Slide<br>1-Stainless Disk |
| 3 | 20 mA-hrs. | $6 \times 10^{-6}$ torr | 1-Glass Slide<br>1-Stainless Disk |

The thickness of each film was determined using a step profiling machine (Sloan-Dektak, Santa Barbara, Calif.). The films were all approximately 5,000 Angstroms (0.5 micron) thick and were translucent as viewed through the coated glass slides. The coated metal pieces had a greenish coloration due to the preferential reflection of green light at the chosen coating thickness. The average sputter rate was 233A/mA-hr. for all three runs.

A scanning electron microscopic (SEM) analysis demonstrated that even under 10,000X magnification, the HA films were essentially featureless, which indicates that they are not porous, have nearly full density and have no grain boundaries.

An elemental X-ray analysis using Edax (Amry, Bedford, Mass.) was performed. The X-rays emitted during the electron examination give an indication of the elements present above the atomic number of sodium. The spectrum of elements detected in the coated titanium foil sample demonstrated that Ti, Al, and V from the metal, as well as P, Cl, and Ca from the HA coating were present. The percentages of phosphorous and calcium (in atomic percents) in the sample film were 32% and 68%, respectively. When a natural apatite standard was analyzed on the same instrument, the values for phosphorous and calcium were 35% and 65%, respectively. This result demonstrates that the process of the present invention is capable of producing a coating which is very close to natural apatite.

A hardness analysis was performed upon the coatings. The mineral HA has a hardness of 5 on the Mohs scale (diamond is 10 and talc is 1 on this scale). Measurements with calibrated scratch points demonstrated that a Mohs 4 probe did not scratch the film, a Mohs 5 probe barely scratched it and a Mohs 6 probe severely scratched it. The hardness is therefore about 5 from this measurement, which is consistent with a fully dense HA.

The adhesion of the HA film to both titanium and stainless steel appeared to be extremely good based on additional scratch tests that were performed. These scratch tests demonstrated no flaking or transverse cracks along the scratch line, even at a 200-fold magnification. This shows that the adhesion to metal is as good or better than the cohesive strength of the coating itself.

EXAMPLE 2

The sputtering apparatus described above in Example 1 was employed using a target of cold pressed HA powder, 2"×4"×⅛", formed at a pressure of 500 psi.

HA films coated on glass and single crystal sodium chloride plates were analyzed by X-ray diffraction in order to ascertain the obtained crystal structure. The results demonstrated that the sputtered films were essentially dense, amorphous HA. However, upon subsequent vacuum annealing in a conventional utility furnace at $10^{-4}$ torr pressure and at temperatures ranging between about 300° C. and about 900° C., for times ranging between about 1 hour and 24 hours, complete crystallization occurred.

EXAMPLE 3

The sputtering apparatus as described above in Example 1 was employed. The target was loosely packed HA powder located in a glass tray and the parts to be coated were electrically insulated from the platter.

During this operation, the Xenon beam was turned on, swept over the target and then turned off. This process was repeated. During the sweep of the Xenon beam a potential of about 400 volts from a commonly available one ampere d.c. power supply source was applied to the parts. The potential was applied so that the current ranged up to 400 ma. while the Xenon beam was directed to the implant and deposition of the powder onto the implant was occurring, and dropped to zero when the Xenon beam was off.

The result of this process was a coating of crystalline HA on the implant instead of an amorphous coating. In addition, the coating was nearly identical in chemical composition to natural HA powder.

The invention has been described in reference to preferred embodiments. Those skilled in the art will appreciate that many additions, substitutions and deletions can be made without departing from the spirit and scope of the invention as claimed below.

What is claimed is:

1. A process for manufacturing a hydroxylapatite-coated implant suitable for implantation into an animal said implant having a fully crystalline hydroxylapatite coating comprising the steps of:

directing a high energy beam, operating at at least 10 kev energy, against a hydroxylpatite target positioned such that HA ions kicked off of the target strike the implant and apply an ion beam sputter coating of hydroxylapatite to said implant, applying a negative potential to said implant material, ranging between about 300 volts and about 1000 volts, while the high energy beam is directed at the target, heating said implant for between about 1 hour and about 24 hours at a temperature of between about 300° C. and about 900° C., conducting said process under a vacuum of less than or equal to $10^{-5}$ torr in the presence of a preselected amount of oxygen gas, and recovering a fully crystalline hydroxylapatite-coated implant.

2. The process of claim 1 wherein said high energy beam comprises a Xenon ion beam.

3. The process of claim 1 wherein said metal implant is sputter-etched prior to said ion beam sputter coating.

4. The process of claim 1 wherein the Xenon ion beam is directed substantially horizontally, the implant material is located above the beam and the target is positioned in the path of the beam such that HA ions are directed up onto the implant material.

5. The process of claim 4 wherein the implant material is located on a water cooled rotating platter.

6. The process of claim 4 wherein said hydroxylapatite target comprises a solid hydroxylapatite coating on a water cooled substrate.

7. The process of claim 4 wherein said hydroxylapatite target comprises a sintered hydroxylapatite coating on a water-cooled substrate.

8. The process of claim 1 wherein said implant material is selected from the group consisting of titanium, titanium alloys, stainless steel and cobalt-chrome-molybdenum.

9. The process of claim 1 wherein said oxygen is present in amounts ranging between about $10^{-5}$ torr and about $10^{-15}$ torr partial pressure.

10. The process of claim 11 wherein said oxygen is present in amounts ranging between about $3\times10^{-6}$ torr and about $5\times10^{-6}$ torr partial pressure.

11. The process of claim 1 wherein said hydroxylapatite target comprises powdered hydroxylapatite located on a water cooled tray.

12. The process of claim 1, wherein said hydroxylapatite-coated implant is first plasma spray coated with titanium before hydroxylapatite coating.

13. A hydroxylapatite-coated implant, suitable for implantation into an animal in need of such treatment, said implant having a fully crystalline hydroxylapatite-coating manufactured by a process comprising the steps of:

directing a high energy beam, operating at least 10 kev energy, against a hydroxylapatite target positioned such that HA ions kicked off of the target strike the implant and apply an ion beam sputter coating of hydroxylapatite to said implant, applying a negative potential to said implant material, ranging between about 300 volts and about 1000 volts, while the high energy beam is directed at the target, heating said implant for between about 1 hour and about 24 hours at a temperature of between about 300° C. and about 900° C.

conducting said process under a vacuum of less than or equal to $10^{-5}$ torr in the presence of a preselected amount of oxygen gas, and recovering a fully crystalline hydroxylapatite-coated implant.

14. The implant of claim 13 wherein the high energy ion beam comprises a Xenon ion beam.

15. The implant of claim 13 wherein the implant is first plasma spray coated with titanium before hydroxylapatite coating.

16. The implant of claim 13 wherein said oxygen is present in amounts ranging between about $10^{-5}$ torr and about $10^{-7}$ torr.

* * * * *